United States Patent
Pelfrey

Patent Number: 5,868,729
Date of Patent: Feb. 9, 1999

[54] SURGICAL PROSTHESIS INSERTION DEVICE

[76] Inventor: Robert J. Pelfrey, 3982 Bee Ridge Rd., Sarasota, Fla. 34233

[21] Appl. No.: 626,439

[22] Filed: Apr. 2, 1996

Related U.S. Application Data

[63] Continuation of Ser. No. 235,563, Apr. 29, 1994, abandoned.
[51] Int. Cl.[6] ............................... A61B 17/00; A61F 5/00
[52] U.S. Cl. .................................................. 606/1; 600/38
[58] Field of Search .................................... 606/139, 148, 606/1, 222, 224, 99, 104, 108, 106, 167, 185; 600/38–41

[56] References Cited

U.S. PATENT DOCUMENTS

| | | |
|---|---|---|
| 3,954,102 | 5/1976 | Buuck . |
| 4,244,370 | 1/1981 | Furlow et al. . |
| 4,350,151 | 9/1982 | Scott . |
| 5,047,039 | 9/1991 | Avant et al. ............................. 606/148 |
| 5,250,054 | 10/1993 | Li ............................................. 606/148 |
| 5,306,240 | 4/1994 | Berry ....................................... 606/18 |
| 5,433,722 | 7/1995 | Sharpe et al. ........................... 606/222 |

FOREIGN PATENT DOCUMENTS

| | | | |
|---|---|---|---|
| 148949 | 4/1992 | European Pat. Off. ............... | 606/148 |

OTHER PUBLICATIONS

*Inflatable Penile Prosthesis: New Device for Cylinder Insertion,* William L. Furlow, M.D., *Urology,* Oct. 1978, vol. XII, No. 4, pp. 447–448.

Medical Products Information Brochure from Lone Star Medical Products, Inc., *The Dilamezinsert Dilates, Measures, and Inserts.*

*Primary Examiner*—Glenn K. Dawson
*Attorney, Agent, or Firm*—Fish & Richardson P.C.

[57] ABSTRACT

A surgical tool includes a malleable elongate body having a flexible plunger rod slidably mounted in a bore therein and having a tapered and rounded forward end for ease of insertion into the body. A needle having suture material attached may be placed into the end of the rod, which can be retracted into the bore of the elongate body. In practice, the tool may be inserted into a bodily structure, such as one of the corpora cavernosum of a penis. The outer surface of the tool body may be equipped with measuring markings to allow the user to gauge the depth that the barrel has been inserted into a bodily structure. After the tool has been malleably bent to access the corpora cavernosa in the desired manner, the flexible plunger rod, with threaded suturing needle attached is slid along the bore to extend the needle out of the rounded, tapered end thereof. The needle is manually pulled out of the bodily structure. After the tool is withdrawn, the suture material remains threaded through the bodily structure.

23 Claims, 3 Drawing Sheets

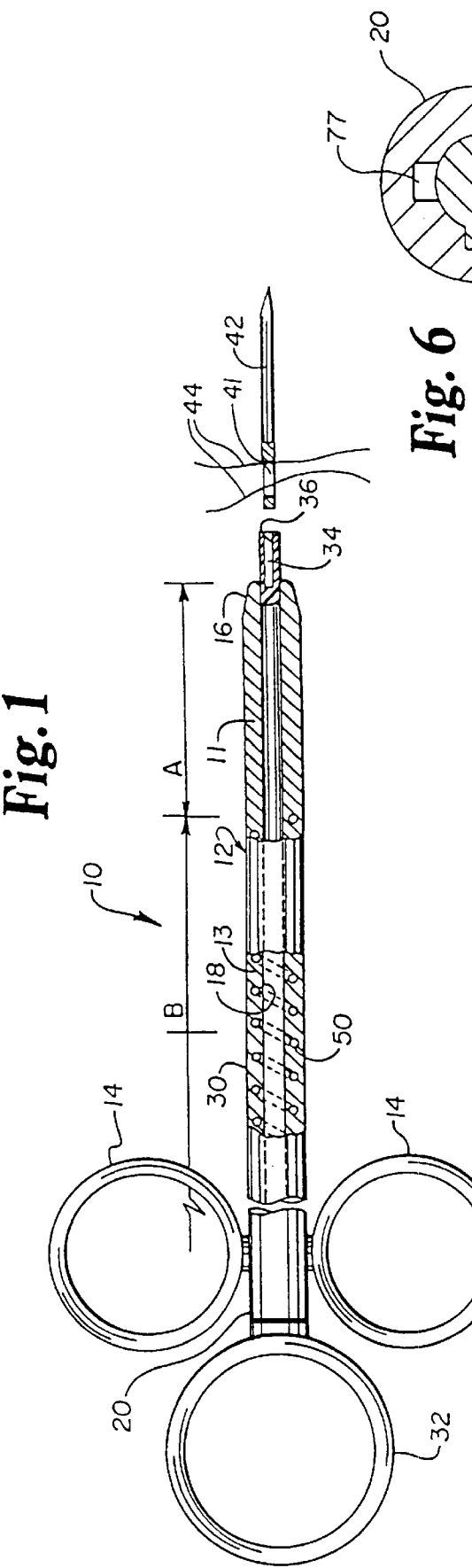
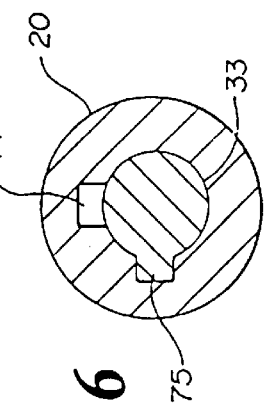
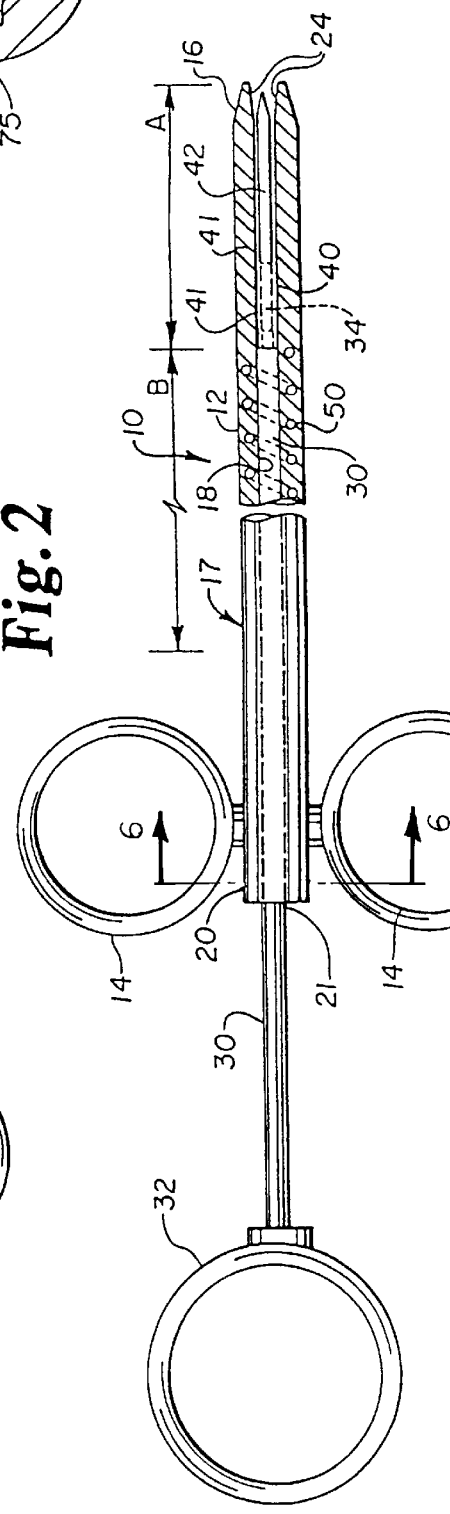
Fig. 1
Fig. 2
Fig. 6

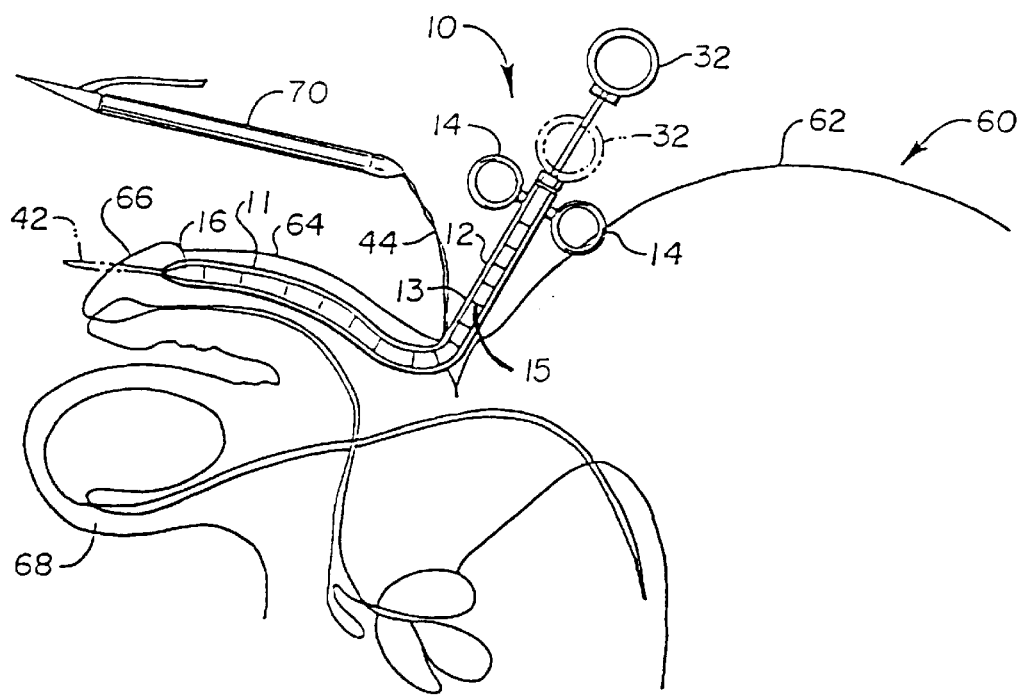
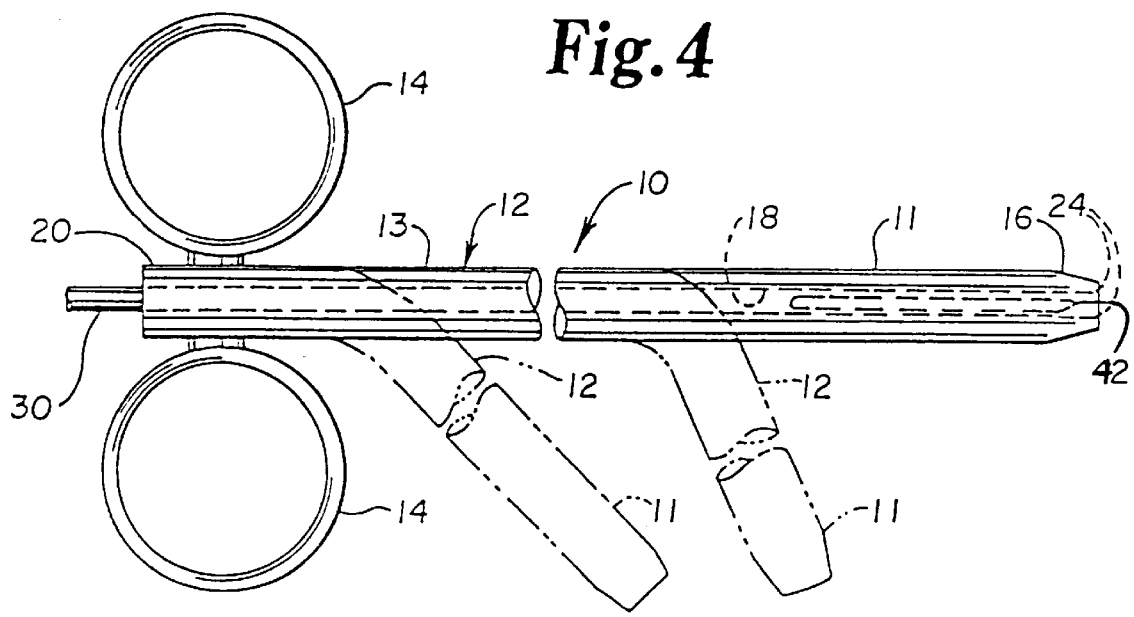

SURGICAL PROSTHESIS INSERTION DEVICE

This application is a continuation of Ser. No. 08/235,563 filed on Apr. 29, 1994, now abandoned, and the benefit of priority under 35 USC §120 is hereby claimed.

BACKGROUND OF THE INVENTION

This invention relates generally to medical devices and pertains more particularly to a surgical tool for the implantation of urological prosthetic devices.

Various techniques and equipment have been developed for the implantation of urological prosthetic devices, using tools such as forceps or dilators. One well known type of prosthetic device which may be implanted using such tools is described by Robert Buuck in U.S. Pat. No. 3,954,102 which discloses a penile erection system. That patent describes the use of a rigid metal rod to dilate the corpora cavernosa regions of the penis to allow insertion of inflatable prosthetic cylinders.

Several other tools have been provided in this art, including one by Scott, U.S. Pat. No. 4,350,151 and another by Furlow and Mikulich, U.S. Pat. No. 4,244,370. Both of these tools, among other things, are used to introduce a suture carrying needle into the penile corpora cavernosa. The Furlow et al. device has overcome many of the undesirable aspects of prior insertion tools and methods. However, the Scott and Furlow et al. tools, as well as other prior art tools, have a disadvantage in that they are rigid, which constricts the maneuverability of the tools when encountering other external bodily obstructions, such as obese abdomens, as is further discussed hereinbelow.

This invention provides a new and improved tool constructed in such a manner and of such materials as to render it flexible and in its most preferred embodiment malleable, and even provides it in a disposable form, thus eliminating the necessity for sterilization of the tool between procedures.

Accordingly, an object of the present invention is to provide an improved tool for implanting medical prosthetic devices and for other medical procedures. The tool has advantages over existing tools in the following areas:

1. Increased ease of passage and insertion of the tool due to its flexibility.
2. Increased control of insertion and position of the suture carrying needle with the ability to retract the needle if the position is not optimal without removing and replacing the instrument with resultant minimization of tissue trauma.
3. Conformity to tissue curves and angles with less chance of a crossover between the septum dividing the corpora cavernosa and/or trauma to the corpus spongiosum tissue.
4. Disposability so there is no chance of contamination due to retained debris from a previous procedure.
5. Positive control of the suture needle with minimal chance of unintentional exposure of the needle.
6. Malleability with resultant greater ease of placement and positioning in cases of anatomical and positional obstructions or abnormalities.

SUMMARY OF THE INVENTION

The invention provides an improved surgical tool for assisting in penile implant surgery and the like. The tool is comprised of a flexible elongate body having a longitudinal bore therethrough. Optionally, the body may also be malleable so as to "hold" a selected configuration when it is bent in use. A flexible plunger rod is slidably received in the bore and is adapted to carry a suture needle at the distal end thereof. Manipulation of the rod at the proximal end of the tool reciprocates it between a retracted position in which the needle is entirely within the distal end of the bore and an extended position in which the needle extends out of the bore. Various additional features are described hereinbelow and/or will be readily apparent.

BRIEF DESCRIPTION OF THE FIGURES

FIG. 1 is a side elevational view of a tool according to the invention showing the rod in the extended mode with partial longitudinal cross sectioning, and a needle being attached thereto;

FIG. 2 is a side elevational view of a tool according to the invention showing the needle in the retracted mode, with partial longitudinal cross sectioning;

FIG. 4 is another side elevational view of the invention, similar to FIG. 3 with different phantom lined malleable configurations shown;

FIG. 4a is a first possible malleable configuration of the invention;

FIG. 4b is a second possible malleable configuration of the invention;

FIG. 5 is a partial diagrammatic side profile view of a human male in a supine position, with the tool of the invention being utilized in one procedural position; and FIG. 6 is a cross-sectional view taken along line 6—6 of FIG. 2 showing an optional feature which may be included.

DETAILED DESCRIPTION OF THE INVENTION

Figure 3:
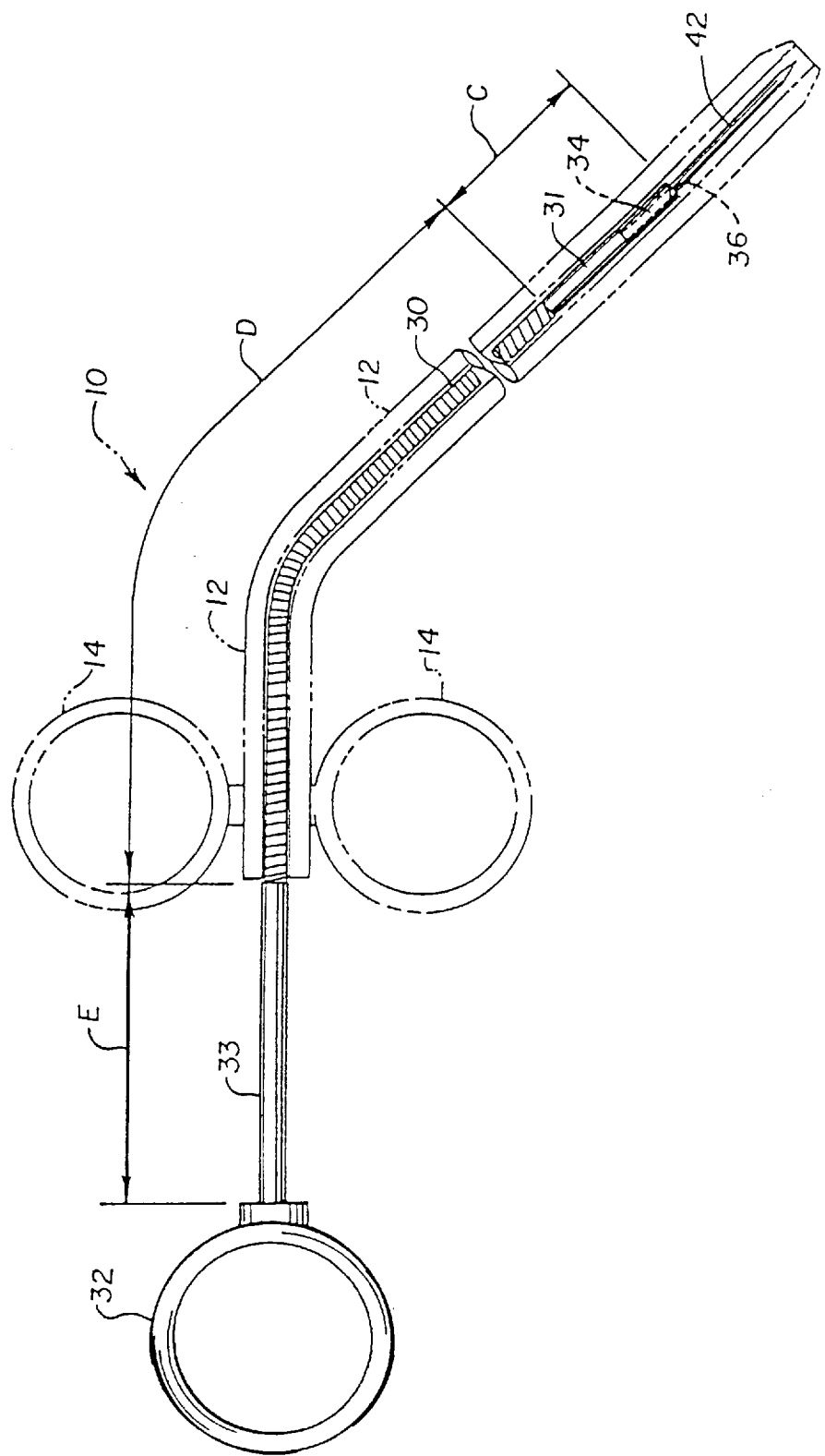
FIG. 3 is a side elevational view of the tool showing it in a "bent" configuration.

Referring now to FIGS. 1 and 2, a preferred embodiment of the invention is designated generally by 10. It is comprised of an elongate, generally cylindrical body 12 with a transversely mounted finger-hole handle 14 at the proximal end for gripping, a rounded and tapered configuration 16 at its distal end for ease of insertion, and having a continuous longitudinal bore 18 running the full length of body 12. Preferably, bore 18 will be coaxial with body 12. At the proximal end of body 12 is a collar 20 by means of which handle 14 may be attached to body 12. Collar 20 may be crimped or otherwise attached in any number of ways to body 12. The interior of bore 18 at the distal end 16 may include a slightly flared orifice 24.

Still referring to FIGS. 1 and 2, the distal portion 11 of body 12 may be constructed and arranged to be of a generally pliable segment of polymeric material (such as a polyurethane, a silicone, polyvinylchloride, or the like), monolithically cast with an even more pliable segment 13, or otherwise for flexibility. The manner of preparing flexible to rigid polymers and elastomers is well known in that art. Other arrangements will be readily apparent for this purpose as well. The longitudinal extent of body portions 11 and 13 is generally indicated by arrows A and B, respectively in the Figures. Body 12 overall may be of the same material having the same pliant or flexible characteristics as well. Also, body 12 may optionally be formed with a winding of malleable wire 50, such as silver, stainless steel or copper, to provide pliable and malleable manipulation of body 12. The malleable metal winding may be encased within the wall of body 12 in configurations other than the winding as shown. For example, longitudinal lengths (not shown) of malleable metal could be included. Other arrangements to this end will be readily apparent.

As best seen in FIG. 3, a flexible plunger rod generally indicated at 30 is slidably received in bore 18 of body 12 for reciprocating motion therein. Plunger rod 30 is flexible over at least a part of its length as is described hereinbelow. The rod may be of a thermoplastic such as polypropylene, polyvinylchloride, polyurethane or the like. It may be more rigid but due to its relatively small diameter will still be flexible enough to function as needed. It has at the proximal end a transversely mounted thumb ring handle 32 for gripping. At the distal end 31 of plunger rod 30 is a tubular opening or lumen 34, the interior of which is of pliant plastic 36 such as silicone rubber for the purpose of grasping the eye portion 41 of a surgical needle 42. The use of pliant plastic 36 for this purpose is presently preferred. However, other arrangements may be made for grasping the needle, such as configuring lumen 34 to receive and retain it by a simple interference fit or the like, for example. Distal end segment 31 of rod 30 which houses lumen 34 and pliant material 36 may be a cylindrical unit of metal which crimps onto a flexible intermediate portion 37 of the rod 30. Other connecting arrangements may be used. The proximal end portion 33 of rod 30 to which gripping ring 32 is attached may also be a tubular metal segment crimped onto the intermediate flexible portion 37 of rod 30. Flexible portion 37 is preferably formed by tightly wound spring metal wire such as stainless steel or the like as shown. However, other flexible arrangements and materials can be used. For example, portion 37 could be of a flexible plastic. The longitudinal extent of segments 31, 37 and 33 is generally indicated by the arrows C, D and E, respectively, in FIG. 3.

Segment 33 of rod 30 has a dual purpose. It's end, at which it connects with flexible portion 37, provides visual orientation (best seen in FIG. 3) when adjacent to the proximal end of body 12 of the position of rod 30 in bore 18 so as to indicate that needle 42 has been fully retracted to the "safe" position enabling body 12 to be properly positioned in the corpora cavernosa without the needle inadvertently piercing the wall thereof. it also provides a rigid portion to depress rod 30 into body 12 without the flexible portion 37 "snaking" as it is depressed to extend the needle from bore 18.

The flexible plunger rod 30 may be fabricated of a metal or a plastic or a metal and plastic combination to allow for flexibility with any surgical angle and allow positive control of the suture needle.

FIG. 1 discloses the plunger rod 30 fully depressed into body 12, with handle 32 seated against the collar 20 of body 12. In this position, lumen 34 protrudes from the distal end of body 12 enabling it to receive the eye portion 41 of a suture needle 42 such as a Keith Needle. Eye portion 41 has been previously threaded with appropriate doubled suture 44 emanating from, for example, an inflatable prosthesis 70 (not shown in this view, see FIG. 5). As sutured eye portion 41, needle 42 is inserted into lumen 34 which is of sufficient diameter and pliability to insure secure grasping of the needle, rod 30 may be withdrawn into body 12. This withdraws needle 42 into the distal end 16 of body 12. When body 12 has been properly positioned at the glans penis, the rod 30 is depressed into the body 12 from the proximal end of the tool to a point at which needle 42 pierces the glans penis at the selected location. The protruding needle 42 is then grasped with a rubber shod forceps and pulled through the opening in the glans. The aforementioned suture 44, being attached to the end of the prosthesis (not shown in these two Figures, see FIG. 5), provide a means with which to position the prosthesis within the corpora cavernosa as is well known to those familiar with this surgical procedure.

Of course, other constructions may be utilized in place of suture needle 42. Any piercing means capable of passing through the glans penis with a suture may be used. For example, the distal end of rod may integrally or other wise include a surgically sharpened point (not shown) which carries the suture. In such an instance, the distal end of rod 30 might be made of annealed stainless steel or the like having an OD of say 0.032 inches. The entire rod could also be of flexible stainless. With such an arrangement, the surgeon would simply remove the ends of the suture from an eye in the rod after it exited the glans. The plunger rod would then be retracted prior to withdrawal of the device from the cavernosum. In such a modified construction and arrangement the distal end of the shaft would not have to be designed to house a retracted Keith needle or the like.

The preceding procedure is generally similar to those presently practiced. However, the flexible and optionally malleable construction of body 12 and flexible rod 30 represent particularly unique features of this invention for improving this procedure.

Referring now to FIG. 4, the solid lines disclose a side elevational view of the invention, while the phantom lines show a plurality of malleable configurations, as shown in FIGS. 4a and 4b of the invention prior to deployment of the surgical needle. It is to be understood, of course, that the malleable bends may be directed up, down, or side to side at any angle, at any location along the malleable portion of the barrel 12 as may be required by the operating surgeon during the insertion procedure. It is also to be understood that the entire tool i.e., body 12 and rod 30 may be flexible over its entire length or only a region or regions over the length may be flexible. The same is true for the malleable feature with respect to body 12.

The utility of flexibility and optional malleability is best demonstrated in FIG. 5, utilizing the infrapubic or suprapubic insertion technique wherein a patient may be overweight, with an excessively protruding abdomen, making it extremely difficult for the surgeon to manipulate a conventional tool such as the Furlow et al., tool or the Scott tool, both of which are rigid from end to end. It should be noted, however, that this invention is also suited for the scrotal approach to insertion of the prosthesis as well. More specifically, FIG. 5 discloses a supine patient generally at 60 with a protruding abdomen 62 in schematic profile outline, with the invention 10 being malleably and flexibly bent for insertion to facilitate optimal positioning of the tool into the corpora cavernosum. Also shown in this view are the penis 64, glans penis 66, scrotum 68, and an inflatable prosthesis 70. The solid lines indicate full retraction of rod 30, while the phantom lines indicate full depression of rod 30 and the needle 42 extending through the glans penis. One of the primary benefits of being able to securely grasp the needle eye portion 41 by plunger rod 30 is that, should the surgeon happen to pierce the glans at an undesirable or inappropriate exiting point, he is able, with this invention, to retract the needle 42, and reposition the barrel 12 by merely retracting the flexible plunger rod 30 and relocating the tool 10.

It should be noted that beginning at the tapered end of body 12 centimeter gradation marks is as shown in FIG. 5, may be stamped thereon to aid the surgeon in determining the depths to which the tool is inserted. This is fairly standard in this art.

Another advantage of this invention is that the entire device may be constructed of materials which render it disposable after use, eliminating the necessity of sterilization for reuse as with the prior art. The combinations of materials already described hereinabove will serve this purpose or the entire device may be of polyvinylchloride or polyurethane, different parts having different flexibility, pliability, rigidity and the like.

Generally, construction may be entirely of medical grade plastics suitable for short term contact with compromised tissue and body fluids. Such elastomers are known and include polyvinylchloride, polyurethane, polypropylene, silicone and the like. Selection of certain elastomers for rod 30 and body 12 may in the case where plastic handles are to be solvent or heat bonded to the body, determined by the plastics to be used for the handles. For example, the use of polyvinylchloride for body 12 and rod 30 may make the use of rigid polyvinylchloride for the handles the best choice of materials combination.

Referring now to FIG. 6, an optional feature is shown which may be included in the device. This feature comprises keying rod 30 to the bore in collar 20 to prevent advancement of rod portion 33 when the thumb ring 32 is not in the same plane as finger grips 14. To this end, a portion of rod portion 33 will include a key 75 which must be rotated to align to a mating opening shape 77 in the bore of collar 20. Other means for this purpose may be used also.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A surgical tool for use by a practitioner during an implant procedure involving the penile corpus cavernosum, said surgical tool being useable with a piercing member and a suture, said surgical tool comprising:

an elongate body, said elongate body having a proximal end, a distal end, and a length measured therebetween, said elongate body being generally flexible over at least a portion of said length such that said elongate body may be selectively manipulated into a desired configuration by the practitioner during the implant procedure, said distal end being adapted for insertion within the penile corpus cavernosum and easing insertion therein, said elongate body further defining a longitudinal bore extending generally along a portion of said length thereof; and a plunger rod, at least a portion of said plunger rod being generally flexible and slidably received within said bore of said elongate body for reciprocating movement therein, following selective manipulation of said elongate body into said desired configuration, said plunger rod adapted to carry the piercing member and a portion of the suture thereon, said plunger rod movable between a retracted position at which the piercing member and said portion of the suture are disposed within said bore adjacent said distal end of said elongate body, and an extended position at which the piercing member is exposed externally to said bore of said elongate body.

2. The surgical tool of claim 1 wherein the elongate body further is malleable such that the elongate body generally retains the desired configuration into which it was selectively flexed by the practitioner until the practitioner manipulates the elongate body to conform to a different configuration.

3. The surgical tool of claim 2 wherein the elongate body further comprises:

a wall formed of an elastomeric material; and a wire winding of malleable metal at least partially encased within said wall and extending over at least a portion of the length of the elongate body.

4. The surgical tool of claim 1 wherein the elongate body is formed from an elastomeric material.

5. The surgical tool of claim 1 wherein the plunger rod is formed over an intermediate length thereof from a flexible material.

6. The surgical tool of claim 5 wherein the flexible material is a metal formed in a generally tight elongate winding.

7. The surgical tool of claim 5 wherein the plunger rod has a proximal end portion and an intermediate portion, said proximal end portion being formed from a material which is less flexible than said intermediate portion thereof such that bowing of the plunger rod is avoided when pressure is applied to the plunger rod to insert it into the bore.

8. The surgical tool of claim 1 wherein the proximal end of the elongate body defines an opening communicating with the bore, the plunger rod has a proximal end portion, and the plunger rod has a length such that said proximal end portion of the plunger rod extends from the proximal end of the elongate body through the opening when the piercing member is in the retracted position, such that a visible indication of the piercing member being retracted is provided to the practitioner.

9. The surgical tool of claim 8 including a marking disposed on the plunger rod for providing the visible indication that the piercing member is in the retracted position.

10. The surgical tool of claim 1 including a gripping member connected to and extending from the proximal end of the elongate body so as to facilitate operation of the plunger rod within the bore by the practitioner.

11. The surgical tool of claim 1 wherein the elongate body and the plunger rod are disposable.

12. The surgical tool of claim 1 wherein the plunger rod has a distal end portion formed from a generally resilient material and defining a recess for receiving and holding the piercing member by a press fit.

13. The surgical tool of claim 12 wherein the piercing member has an eye and the suture is a double suture, and wherein the recess is sized to accommodate the piercing member with said double suture placed within said eye.

14. The surgical tool of claim 1 wherein the plunger rod and the elongate body further comprise:

a mechanism connected to the surgical tool for preventing the unintentional advancement of the plunger rod within the bore of the elongate body such that the piercing member is moved to the extended position.

15. The surgical tool of claim 1, in combination with a piercing member comprising:

a suture needle mounted on and carried by the plunger rod and extending therefrom.

16. The surgical tool of claim 1 further comprising:

an indicator operatively connected to the plunger rod to indicate to the practitioner whether the piercing member is retracted.

17. The surgical tool of claim 16 wherein the indicator provides a visible indication.

18. The surgical tool of claim 16 further comprising:
a grip member connected to and extending from the proximal end of the elongated body, the indicator providing a visual indication to the practitioner whether the piercing member is in the retracted position.

19. A surgical tool for use by a practitioner during an implant procedure involving the penile corpus cavernosum, said surgical tool being useable with a piercing member and a suture, said surgical tool comprising:

an elongate body, said elongate body having a proximal end, a distal end, and a length measured therebetween, said elongate body being generally flexible over at least a portion of said length such that said elongate body may be selectively manipulated into a desired configuration by the practitioner during the implant procedure, said elongate body further being generally malleable such that said elongate body generally retains said desired configuration until the practitioner manipulates the elongate body to conform to a different configuration, said distal end being adapted for insertion within the penile corpus cavernosum and having a partially enclosed portion for receiving the piercing member; and a reciprocating member, said reciprocating member being operatively connected to said elongated body and adapted to carry the piercing member thereon, said reciprocating member moving between a retracted position at which the piercing member is disposed within said partially enclosed portion of the elongate body generally preventing contact with the penile corpus cavernosum, and an extended position at which the piercing member is exposed external to said partially enclosed portion of the elongate body, said reciprocating member being generally flexible over at least a portion thereof such that following manipulation of said elongate body into said desired configuration, said reciprocating member reciprocates therein between said retracted position and said extended position.

20. The surgical tool of claim 19 further comprising:
a mechanism connected to the surgical tool for selectively preventing the advancement of the reciprocating member relative to the partially enclosed portion of the elongate member such that the piercing member is not inadvertently moved to the extended position.

21. The surgical tool of claim 19 further comprising:
an indicator operatively connected to the reciprocating member to indicate to the practitioner whether the piercing member is in the retracted position.

22. The surgical tool of claim 21 wherein the indicator provides a visible indication.

23. The surgical tool of claim 21 further comprising:
a grip member connected to and extending from the proximal end of the elongated body, the indicator providing are visible indication to the practitioner whether the piercing member is in the retracted position.

* * * * *